(12) United States Patent
Caron et al.

(10) Patent No.: US 6,486,325 B1
(45) Date of Patent: Nov. 26, 2002

(54) PROCESS FOR THE PREPARATION OF PIPERIDINYLAMINOMETHYL TRIFLUOROMETHYL CYCLIC ETHER COMPOUNDS

(75) Inventors: Stéphane Caron, Stonington, CT (US); Enrique Vasquez, South Plainfield, NJ (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/690,346

(22) Filed: Oct. 17, 2000

Related U.S. Application Data
(60) Provisional application No. 60/160,226, filed on Oct. 18, 1999.

(51) Int. Cl.[7] .............................................. C07D 405/12
(52) U.S. Cl. ...................................... 546/196; 546/207
(58) Field of Search ................................. 546/196, 207

(56) References Cited

FOREIGN PATENT DOCUMENTS

WO    WO9925714    10/1998

*Primary Examiner*—Patricia L. Morris
(74) *Attorney, Agent, or Firm*—Peter C. Richardson; Paul H. Ginsburg; Roy F. Waldron

(57) ABSTRACT

The present invention relates to a novel process for the preparation of a diastereomeric mixture of piperidinylaminomethyl trifluoromethyl cyclic ether compounds of formulae Ia and Ib:

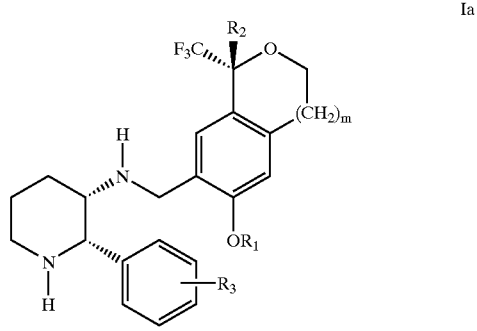

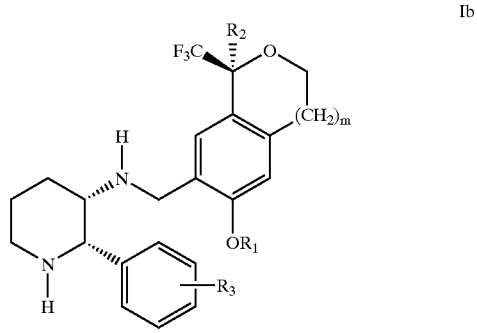

and pharmaceutically acceptable salts thereof, wherein $R^1$ is $C_1$–$C_6$ alkyl; $R^2$ is $C_1$–$C_6$ alkyl, halo $C_1$–$C_6$ alkyl or phenyl or substituted phenyl; $R^3$ is hydrogen or halo; m is zero, one or two, and wherein said mixture is highly enriched in the compound of formula Ia, and to novel processes for the preparation and purification of intermediate compounds useful in the preparation of compounds of formulae Ia and Ib.

5 Claims, No Drawings

PROCESS FOR THE PREPARATION OF PIPERIDINYLAMINOMETHYL TRIFLUOROMETHYL CYCLIC ETHER COMPOUNDS

The application claims the benefit of U.S. provision patent application Ser. No. 60/160,226, filed Oct. 18, 1999.

The present invention relates to a novel process for the preparation of a diastereomeric mixture of piperidinylaminomethyl trifluoromethyl cyclic ether compounds of formulae Ia and Ib:

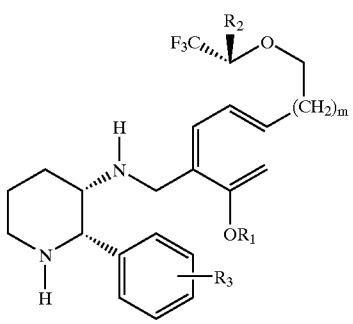

Ia

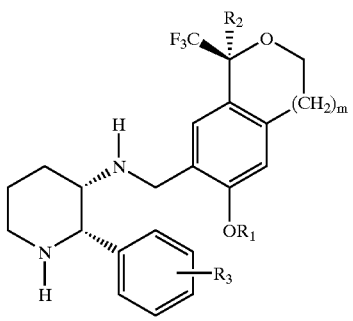

Ib and pharmaceutically acceptable salts thereof, wherein $R^1$ is $C_1$–$C_6$ alkyl;

$R^2$ is $C_1$–$C_6$ alkyl, halo $C_1$–$C_6$ alkyl or phenyl or substituted phenyl;

$R^3$ is hydrogen or halo;

m is zero, one or two.

Further, the present invention also relates to a process for the preparation of a diastereomeric mixture of compounds of formulae Ia and Ib, and pharmaceutically acceptable salts thereof, highly enriched in the compound of formula Ia. The process of the present invention permits via selective crystallization the isolation of diastereomeric mixtures of compounds of formula Ia and Ib wherein the ratio of compounds of formula Ia to Ib are in excess of 90:10.

In addition, the present invention relates to novel processes for the preparation of a compound of formula II:

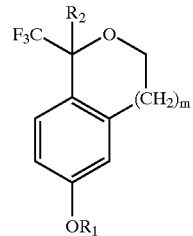

(II)

an intermediate compound useful in the preparation of compounds of formulae Ia and Ib. In addition, the present invention is also directed to other novel intermediates useful in the process for preparing the mixture of compounds of formulae Ia and Ib. The present invention is also directed to a novel process for the purification of certain intermediates for use in the methods of the invention.

The compounds of formula Ia and Ib, particularly compounds of formula Ia, and pharmaceutically acceptable salts thereof, are useful as antagonists of substance P, a naturally-occurring undecapeptide belonging to the tachykinin family of peptides that is widely involved in the pathophysiology of numerous diseases, including central nervous system disorders such as depression, anxiety and schizophrenia, in respiratory and inflammatory diseases such as asthma and rheumatoid arthritis, in gastrointestinal disorders and diseases of the GI tract such as ulcerative colitis and Crohn's disease, and in the transmission of pain, including migraine.

The diastereomeric mixture of compounds of formulae Ia and Ib and a process of making that diastereomeric mixture are described in International Patent Publication No. WO 99/25714, published May 27, 1999. That reference refers to methods of preparing the diastereomeric mixture using methods other than those of the present invention, and is hereby incorporated by reference in its entirety. The present invention provides a more practical, more direct and higher yielding process for preparing a mixture of diastereomers of compounds of formulae Ia and Ib, highly enriched in the compound of formula Ia, via novel synthetic pathways.

SUMMARY OF THE INVENTION

The present invention relates to a process for the preparation of a mixture of compounds of formulae Ia and Ib:

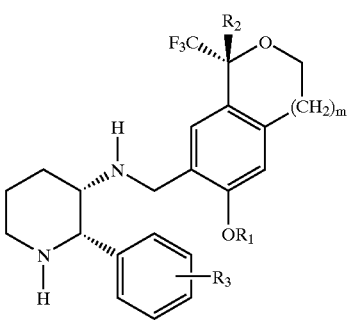

Ia

-continued

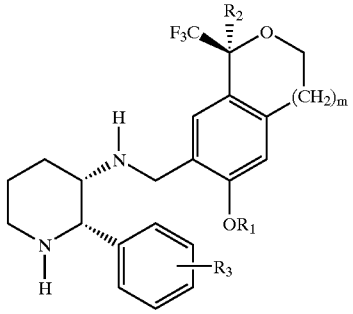

Ib

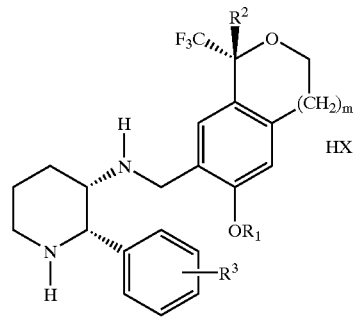

Va

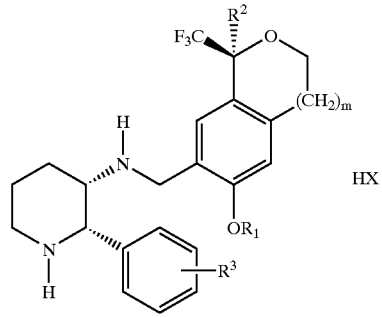

Vb highly enriched in the presence of the compound of formula Ia, and pharmaceutically acceptable salts thereof, wherein $R^1$ is $C_1$–$C_6$ alkyl;

$R^2$ is $C_1$–$C_6$ alkyl, halo $C_1$–$C_6$ alkyl or phenyl or substituted phenyl;

$R^3$ is hydrogen or halo;

m is zero, one or two;

comprising the steps of (a1) reacting a mixture of compounds of formulae Ia and Ib:

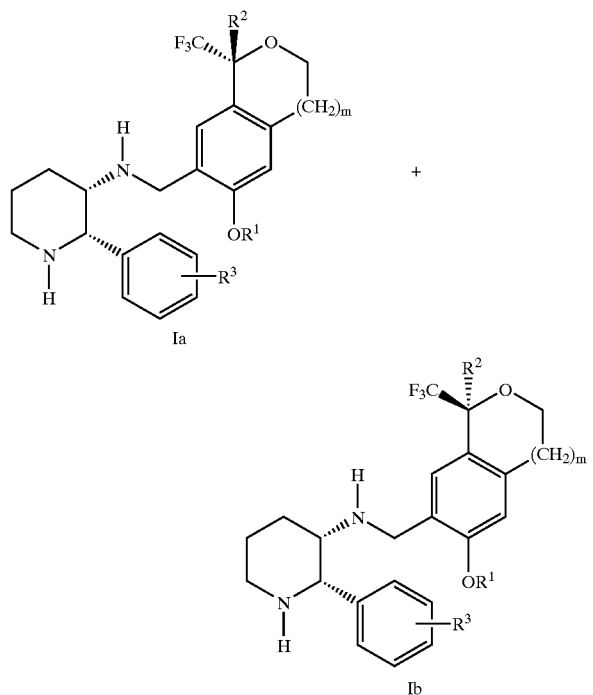

with an acid of formula HX, wherein HX is selected from the group consisting of (S)-(+)-mandelic acid, D-(−)-tartaric acid, di-p-toluoyl-D-tartaric acid, ((1R)-endo,anti)-(+)-3-bromocamphor-8-sulfonic acid, quinic acid, acetic acid and hydrobromic acid, to form a mixture of diastereomeric compounds of formulae Va and Vb, respectively, enriched in the presence of a compound of formula Va:

(b1) permitting the HX salt of the diastereomeric product mixture of step (a1) to crystallize out of a solution thereof in an appropriate solvent; and (c1) treating the resulting mixture of compounds obtained from step (c1) with a base.

A most preferred embodiment of the invention is where the acid HX of step (a1) is (S)-(+)-mandelic acid. A more preferred embodiment of the invention is where the appropriate solvent of step (a1) is selected from the group consisting of methanol, ethanol, isopropanol, tetrahydrofuran, ethyl acetate, isopropyl acetate, methyl-tert-butyl ether, diisopropyl ether, toluene, acetonitrile, acetone, water and a mixture of any of the foregoing solvents. A most preferred embodiment is where the appropriate solvent of step (a1) is ethanol. A more preferred embodiment of the invention is where the base of step (c1) is selected from the group consisting of sodium hydroxide, potassium hydroxide, sodium carbonate, sodium bicarbonate, potassium carbonate and potassium bicarbonate.

The present invention also relates to the preparation of the pharmaceutically acceptable salts of the mixture of compounds of formula Ia and Ib, highly enriched in the compound of formula Ia, which comprises treating the mixture of compounds Ia and Ib that is enriched in one of the diastereomeric compounds of formula Ia with a proton acid, $H^+Y^-$, wherein the anion, $Y^-$, is selected from the group consisting of hydrochloride, hydrobromide, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)), to form a mixture of compounds VIa and VIb, highly enriched in the diastereomeric compound acid addition salt of formula VIa:

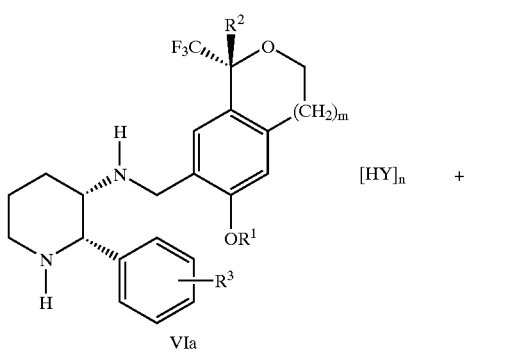

VIa

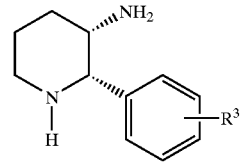

[HY]$_n$ +

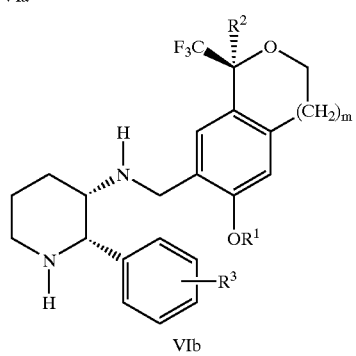

VIb wherein n is determined by the intrinsic characteristics of the form of the compounds Ia and Ib when complexed with the particular acid HY, and n is an integer from one to two. The process of the invention also relates to the preparation of the hydrates of the compounds of formula VIa and VIb, in which between zero and three molecules of water may be associated with each molecule of the compounds of formula VIa and VIb, said hydrates being formed in the step in which compounds of formula Ia and Ib are treated with a proton acid.

A more preferred embodiment of the invention is where the proton acid used is hydrochloric acid, and n is 2. A preferred embodiment of the invention is where the ratio of compound VIa and VIb obtained is 90:10 or greater. A more preferred embodiment of the invention is where the ratio of compound VIa and VIb obtained is 98:2 or greater.

The present invention also relates to a process for the preparation of compounds of formulae Ia and Ib, highly enriched in the presence of a compound of formula Ia, further comprising the step of reacting a compound of formula III:

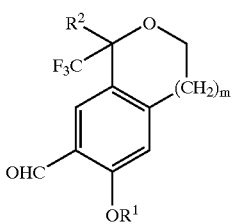

III with a compound of formula IV:

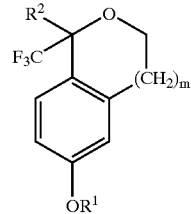

IV in the presence of a reducing agent to obtain a mixture of compounds of formula Ia and Ib.

A preferred embodiment of the invention is where the reducing agent is selected from the group consisting of sodium triacetoxyborohydride, sodium cyanoborohydride and sodium borohydride. A more preferred embodiment of the invention is where the reducing agent is sodium triacetoxyborohydride.

The present invention also relates to the process for the preparation of compounds of formulae Ia and Ib, highly enriched in the presence of a compound of formula Ia, further comprising the step of formylating a compound of formula II:

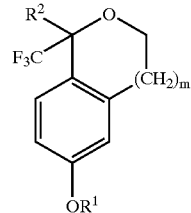

II wherein $R^1$, $R^2$ and $R^3$ are as defined above; m is 0, 1 or 2 with hexamethylenetetramine, in the presence of an acid to form a compound of formula III. A preferred embodiment of the invention is where the acid in the formylation reaction is trifluoroacetic acid, glyceroboric acid, acetic acid or hydrochloric acid. The most preferred acid is trifluoroacetic acid.

The present invention also relates to the process for the preparation of compounds of formulae Ia and Ib, highly enriched in the presence of a compound of formula Ia, wherein the compound of formula II:

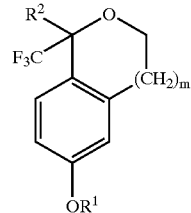

II wherein $R^1$, $R^2$ and $R^3$ are as defined above; m is 0, 1 or 2; is prepared by a process comprising the steps of (a2) reacting a compound of formula VII:

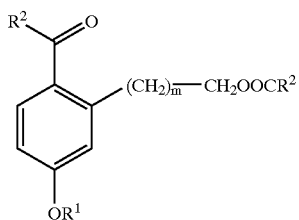

VII with a compound of formula $CF_3SiR^4{}_3$, wherein $R^4$ is $(C_1-C_6)$alkyl or phenyl, in the presence of a fluoride source to form a compound of formula VIII:

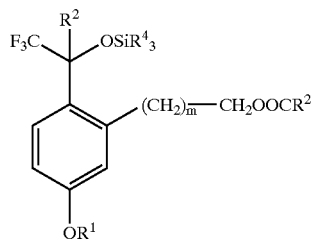

VIII (b2) removing the silyl protecting group from the product of step (a2) via treatment with a base or a fluoride source to form a compound of formula IX:

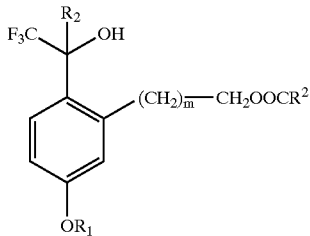

IX (c2) hydrolyzing the ester group of the product of step (b2) in the presence of a base to form a compound of formula X:

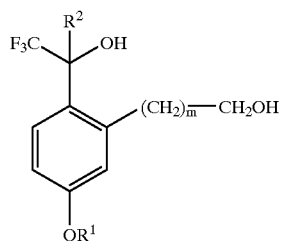

X and (d2) performing a ring cyclization reaction on the product of step (c2) in the presence of a base and an activating agent selected from the group consisting of methanesulfonyl chloride, methanesulfonic anhydride, p-toluenesulfonyl chloride, p-toluenesulfonic anhydride and triflic anhydride.

A more preferred embodiment of the present invention is where the fluoride source in step (a2) is selected from the group consisting of cesium fluoride, potassium fluoride and an alkylammonium fluoride. The most preferred alkylammonium fluoride is tetrabutylammonium fluoride. A most preferred embodiment of the invention is where the fluoride source in step (a2) is cesium fluoride. Preferred solvents for step (a2) are dimethylformamide, dimethylacetamide, toluene, dichloromethane, dichloroethane and tetrahydrofuran. The most preferred solvent for step (a2) is dimethylformamide.

In step (b2), the preferred bases are sodium hydroxide or potassium hydroxide, and the preferred fluoride sources are tetrabutylammonium fluoride, cesium fluoride, hydrofluoric acid-pyridine complex and hydrofluoric acid. The most preferred fluoride source is tetrabutylammonium fluoride. Preferred solvents for step (b2) are tetrahydrofuran, diisopropyl ether, acetonitrile, methyl-tert-butyl ether, dichloromethane and toluene. The most preferred solvent for step (b2) is tetrahydrofuran.

The preferred bases in step (c2) are sodium hydroxide, potassium hydroxide, sodium carbonate, sodium bicarbonate, potassium carbonate and potassium bicarbonate. The preferred base in step (c2) is sodium hydroxide. Preferred solvents for step (c2) are water, tetrahydrofuran, methanol, ethanol, isopropanol, 1,4-dioxane and a combination of any of these solvents. The most preferred solvent for step (c2) is a mixture of water and tetrahydrofuran.

In step (d2), the most preferred activating agent is methanesulfonyl chloride. Preferred bases for step (d2) are triethylamine, diisopropylethylamine, 2,6-lutidine, pyridine, sodium hydroxide, potassium hydroxide, cesium carbonate and potassium carbonate. The most preferred base for step (d2) is triethylamine. Preferred solvents for step (d2) are dichloromethane, tetrahydrofuran, toluene, diisopropyl ether and methyl-tert-butyl ether. The most preferred solvent for step (d2) is dichloromethane.

The present invention also relates to the process for the preparation of compounds of formulae Ia and Ib, highly enriched in the presence of a compound of formula Ia, wherein the compound of formula II:

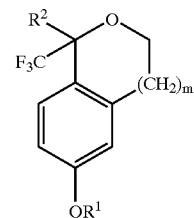

II wherein $R^1$, $R^2$ and $R^3$ are as defined above; m is 0, 1 or 2; comprising the steps of (a3) reacting a compound of formula XI:

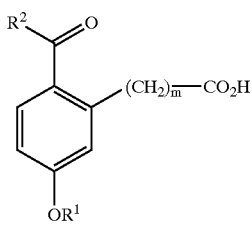

XI with an alcohol of formula $R^1OH$ in the presence of an acid, wherein $R^1$ is as defined above, to form a compound of formula XII:

XII

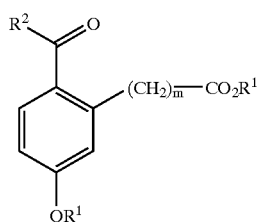

(b3) reacting the product of step (a3) with compound of formula $CF_3SiR^4_3$, wherein $R^4$ is $(C_1-C_6)$alkyl or phenyl, to form a compound of formula XIII:

XIII

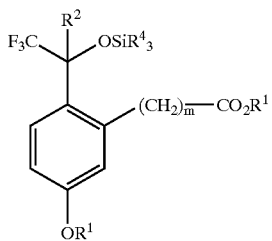

(c3) reacting the product of step (b3) with a fluoride source to obtain a lactone compound of formula XIV:

XIV

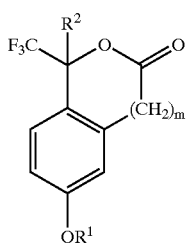

(d3) reacting the lactone product of step (c3) with a reducing agent optionally in the presence of a Lewis acid to obtain a compound of formula XV:

XV

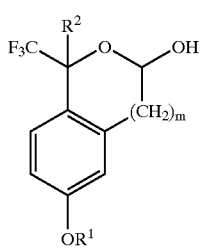

and (e3) reacting the product of step (d3) with a reducing agent optionally in the presence of a Lewis acid to obtain a compound of formula II.

Another preferred embodiment of the invention is where the acid of step (a3) is chosen from the group consisting of sulfuric acid, hydrochloric acid, hydrobromic acid, trifluoroacetic acid and methanesulfonic acid. The most preferred acid for step (a3) is sulfuric acid.

In step (b3), preferred fluoride sources are cesium fluoride, potassium fluoride and an alkylammonium fluoride, such as tetrabutylammonium fluoride. The most preferred fluoride source is cesium fluoride. Preferred solvents for step (b3) are dimethylformamide, dimethylacetamide, dichloromethane and tetrahydrofuran. The most preferred solvent for step (b3) is dimethylformamide.

Preferred fluoride sources for step (c3) are tetrabutylammonium fluoride, cesium fluoride, hydrofluoric acid-pyridine complex and hydrofluoric acid. The most preferred fluoride source for step (c3) is tetrabutylammonium fluoride. Preferred solvents for step (c3) are tetrahydrofuran, diisopropyl ether, acetonitrile, methyl-tert-butyl ether, dichloromethane and toluene. The most preferred solvent for step (c3) is tetrahydrofuran.

Preferred reducing agents for step (d3) are sodium borohydride, borane tetrahydrofuran complex, borane dimethylsulfide complex, diborane, lithium borohydride, calcium borohydride, lithium aluminum hydride, diisobutylaluminum hydride, L-selectride and K-selectride. The most preferred reducing agent is sodium borohydride. The preferred Lewis acid for step (d3) is boron trifluoride diethyl ether complex. Preferred solvents for step (d3) are tetrahydrofuran, diisopropyl ether, methyl-tert-butyl ether and dimethoxyethane. The most preferred solvent for step (d3) is tetrahydrofuran.

The preferred reducing agents for step (e3) are triethylsilane or triphenylsilane, in the presence of a Lewis acid such as boron trifluoride etherate or trifluoroacetic acid, preferably trifluoroacetic acid. Preferred solvents for step (e3) are dichloromethane, dichloroethane and chloroform. The most preferred solvent for step (e3) is dichloromethane.

Another preferred embodiment is where in step (e3) a compound of formula XIV is treated with a catalyst such as platinum, platinum oxide, or palladium hydroxide, preferably platinum, in a solvent such as methanol, ethanol, or isopropanol, preferably ethanol, under an atmosphere of hydrogen, optionally under pressure greater than atmospheric pressure.

The present invention also relates to the process for the preparation of compounds of formulae Ia and Ib, highly enriched in the presence of a compound of formula Ia, wherein the compound of formula III:

III

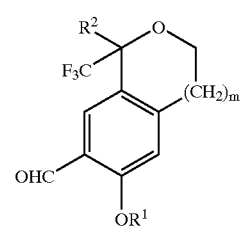

is purified by a method comprising the steps of (a4) forming a hydrazone via the reaction of a compound of formula III with a hydrazone of formula XVI:

XVI $$\underset{NH_2NH}{\overset{R^1}{\bigodot}}\overset{}{SO_2}$$

in the presence of an acid to afford a compound of formula XVII:

XVII

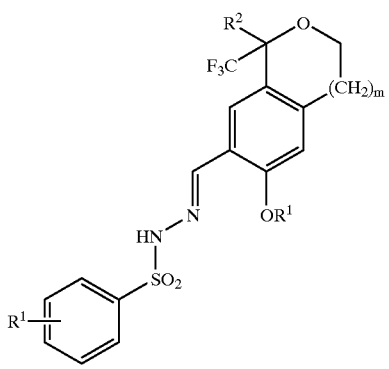

and (b4) hydrolyzing the product of step (a4) via treatment with a reagent selected from the group consisting of copper (II) chloride, copper(II) iodide, copper(II) acetate, copper sulfate, sulfuric acid, acetic acid and hydrochloric acid.

Preferred acids for step (a4) include acetic acid, sulfuric acid, hydrochloric acid, methanesulfonic acid and p-toluenesulfonic acid. The most preferred acid for step (a4) is acetic acid. Preferred solvents for step (a4) are methanol, ethanol, isopropanol, tetrahydrofuran, water and a mixture of any of the foregoing solvents. The most preferred solvent for step (a4) is a mixture of methanol and water.

The more preferred reagent for step (b4) is copper(II) chloride. Preferred solvents for step (b4) are tert-butyl alcohol, methanol, ethanol, isopropanol, tetrahydrofuran, water and a mixture of any of the forgoing solvents. The most preferred solvent for step (b4) is a mixture of tert-butyl alcohol and water.

In addition, methods for the preparation of pharmaceutical compositions of mixtures of the compounds of formula Ia or Ib or pharmaceutically acceptable salts thereof are encompassed by the present invention. A method for the preparation of such a pharmaceutical composition comprises the addition of a mixture of compounds of formula Ia and Ib or pharmaceutically acceptable salts thereof to a pharmaceutically acceptable carrier or diluent.

The present invention is also directed to the novel intermediates used in the methods of the invention, including but not limited to those compounds of formula VII, IX, XIII, XIV, XV and XVII and salts thereof.

The term "alkyl", as used herein, unless otherwise indicated, includes saturated monovalent hydrocarbon radicals having straight, branched or cyclic moieties or combinations thereof.

The term "substituted phenyl", as used herein, unless otherwise indicated, means phenyl substituted by one or more, preferably one or two substituent(s) such as halogen, hydroxy, $(C_1-C_6)$alkyl or $(C_1-C_6)$alkoxy.

The term "halo" or "halogen", as used herein, unless otherwise indicated, means fluorine, chlorine, bromine or iodine.

The term "suitable solvent" or "appropriate solvent", as used herein, unless otherwise indicated, means a medium which serves to dissolve particular indicated substance(s), compound(s) or reagent(s) to form a uniformly dispersed mixture of that substance or compound at the molecular or ionic level.

The term "proton acid" used to prepare acid addition salts of the compounds of the process of this invention are those which form non-toxic acid addition salts, i.e., salts containing pharmacologically acceptable anions, such as the hydrochloride, hydrobromide, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The term "enriched", as used herein, unless otherwise indicated, means to predominate in a ratio of greater than 1:1 of one particular compound or isomer over another or other components in a mixture. The term "highly enriched", as used herein, unless otherwise indicated, means to predominate in a ratio of at least 90:10 of one particular compound or isomer over another or other component in a mixture. Unless otherwise indicated, this invention relates to all optical isomers, tautomers and stereoisomers of the any of compounds described herein.

The term "pharmaceutically acceptable salt", as used herein, unless otherwise indicated, refers to an acid addition salt of a proton acid, as defined herein, or a hydrate of an acid addition salt.

DETAILED DESCRIPTION OF THE INVENTION

A diastereomeric mixture of piperidinylaminomethyl trifluoromethyl cyclic ether compounds of formulae Ia and Ib, highly enriched in a compound of formula Ia, may be prepared in accordance with the novel method shown in reaction scheme 1 below. Novel methods for the preparation of a critical intermediate in the preparation of piperidinylaminomethyl trifluoromethyl cyclic ether compounds, a compound of formula II, may be carried out in accordance with schemes 2 and 3, below. A novel means for purifying a key intermediate in the process of scheme 1 is shown in scheme 4. Unless otherwise indicated, the variables $R^1$, $R^2$, $R^3$, $R^4$, m and n are as described above.

Step 1 of scheme 1 is a formylation. A compound of formula II is treated with hexamethylenetetramine, in the presence of an acid such as trifluoroacetic acid, glyceroboric acid, acetic acid or hydrochloric acid, preferably trifluoroacetic acid, optionally in a solvent such as dichloromethane, dichloroethane, heptane, or nitromethane, preferably without a solvent at a temperature between 0 and 100° C., preferably at 70° C., for a period of time between 10 minutes and 24 hours, preferably 3 hours, followed by addition of water, to afford a compound of formula III. At this point, the compound of formula III may be purified according to the method of the invention as set forth below at scheme 4 prior to proceeding with step 2.

Step 2 of scheme 1 is a reductive coupling. An aldehyde of formula III is treated with an amine of formula IV, or a salt thereof, in the presence of a reducing agent, such as sodium triacetoxyborohydride, sodium cyanoborohydride, or sodium borohydride, preferably sodium triacetoxyborohydride, in a solvent, such as dichloromethane, dichloroethane, tetrahydrofuran, toluene, acetic acid, diisopropyl ether, or methyl-tert-butyl ether, preferably dichloromethane, at a temperature between −20 and 60° C., preferably 0° C., for a period of time between 30 minutes and 24 hours, preferably 3 hours, to afford a mixture of compounds of formulae Ia and Ib.

Scheme 1

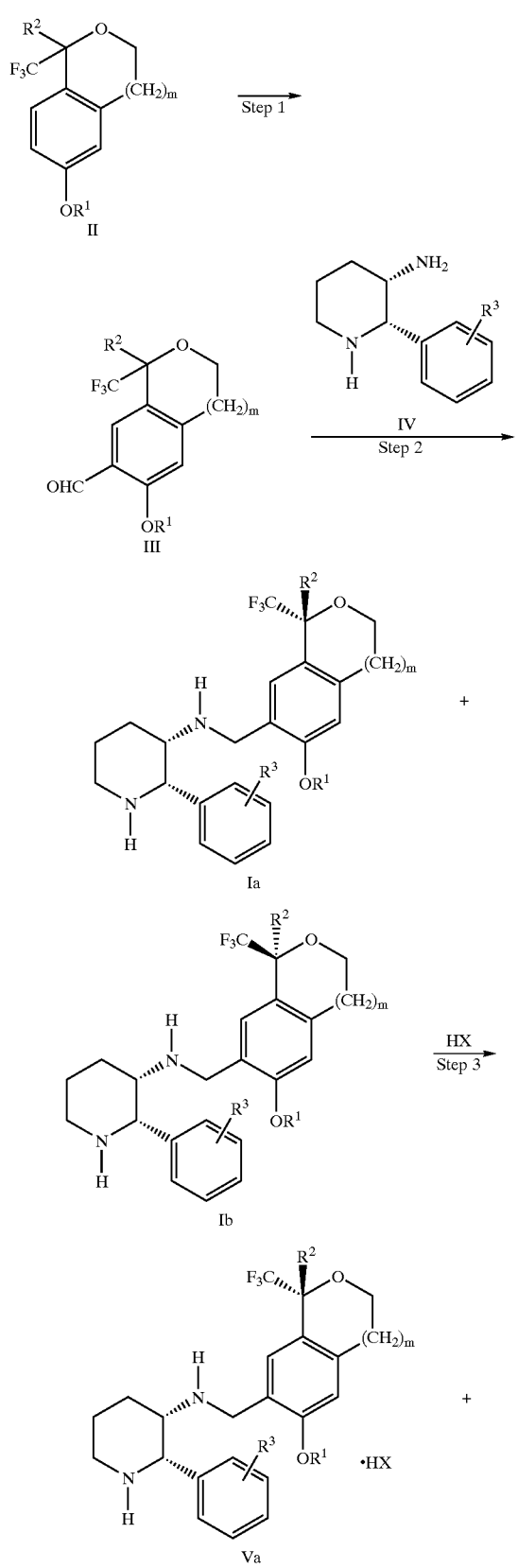

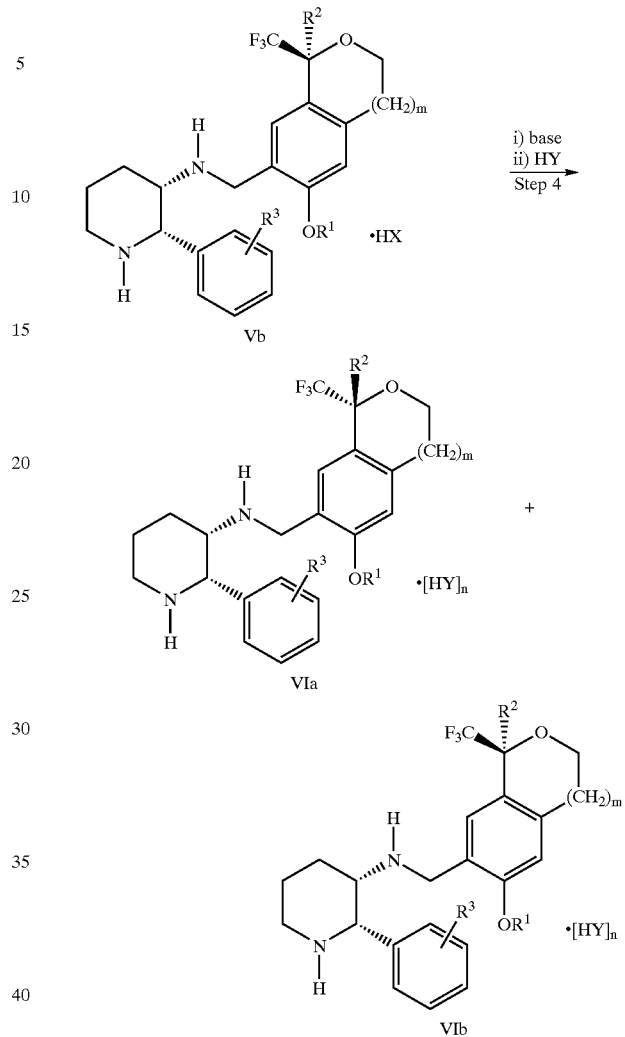

Step 3 of scheme 1 is a salt formation. The mixture of compounds Ia and Ib is treated with an acid of formula HX, such as (S)-(+)-mandelic acid, D-(−)-tartaric acid, Di-p-toluoyl-D-tartaric acid, ((1R)-endo,anti)-(+)-3-bromocamphor-8-sulfonic acid, quinic acid, acetic acid, hydrobromic acid, preferably (S)-(+)-mandelic acid, in a solvent, such as methanol, ethanol, isopropanol, tetrahydrofuran, ethyl acetate, isopropyl acetate, methyl-tert-butyl ether, diisopropyl ether, toluene, acetonitrile, acetone, water, or a mixture of the foregoing solvents, preferably ethanol, at a temperature between −20 and 70° C., preferably room temperature, for a period of time between 30 minutes and 48 hours, preferably 18 hours, to afford a mixture of compounds of formula Va and Vb which is enriched in compound of formula Vb. Step 3 permits the isolation of mixtures of compounds of formula Va and Vb wherein the ratio of compounds of formula Va to Vb is greater than 70:30, and generally 80:20 or greater.

Step 4 of scheme 1 is the formation of an acid addition salt. The mixture of compounds of formula Va and Vb highly enriched in compound Va is treated with a base such as sodium hydroxide, potassium hydroxide, sodium carbonate, sodium bicarbonate, potassium carbonate or potassium bicarbonate, in water in the presence of a cosolvent such as toluene, diisopropyl ether, methyl-tert-butyl ether, ethyl acetate, or dichloromethane, preferably diisopropyl ether, at a temperature between 0 and 40° C., preferably room temperature, for a period of time between 10 minutes and 48 hours, preferably 18 hours, to afford a mixture of compounds of formula Ia and Ib which is enriched in compound of formula Ia. The ratio of compound Ia to Ib, obtained from this part of step 4 is 70:30 or greater, but in general 80:20 or greater. This mixture is treated with a proton acid, HY, as defined above, preferably hydrochloric acid, in a solvent, such as methanol, ethanol, isopropanol, tetrahydrofuran, diisopropyl ether, water or a mixture of the foregoing solvents, preferably a mixture of methanol and water, at a temperature between 0 and 60° C., preferably room temperature, for a period of time between 1 hour and 48 hours, preferably 18 hours, to afford a mixture of compounds of formula VIa and VIb which is highly enriched in compound of formula VIa, and wherein n is as defined above. Step 4 permits the isolation of mixtures of compounds of formula VIa and VIb wherein the ratio of compounds of formula VIa to VIb are greater than 90:10, and may approach 98:2 or better. Step 4 may be repeated to obtain higher ratios if needed.

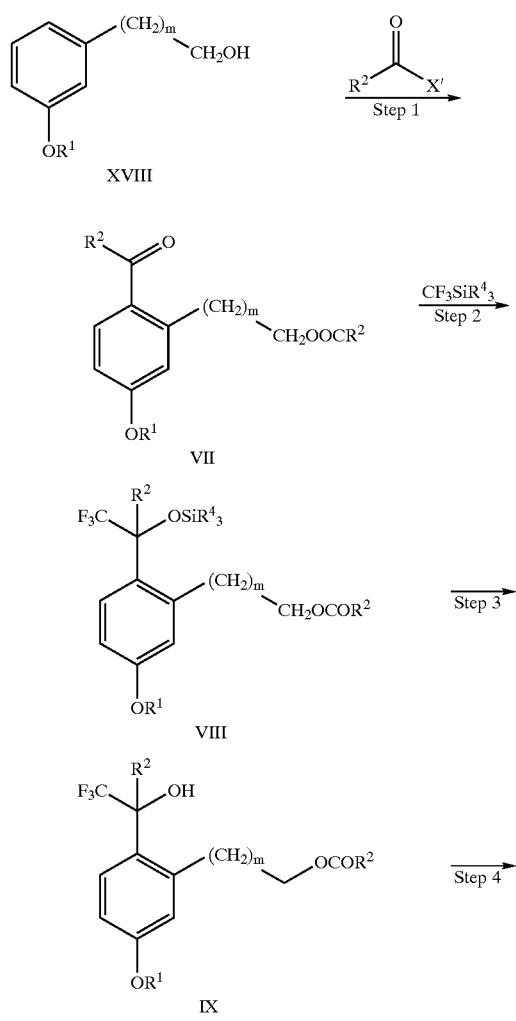

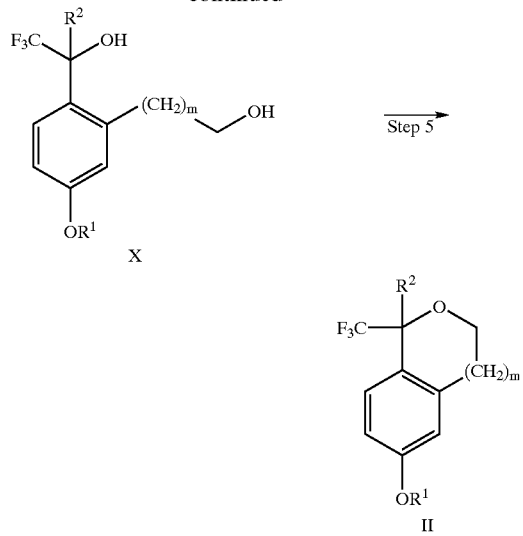

Step 1 of scheme 2 is an acylation of an arene which proceeds with protection of an alcohol in a way similar to a known procedure (Sternberg, E. D.; Vollhardt, K. P. C. *J. Org. Chem.* 1984, 49, 1574–1583). An arene of formula XVIII is treated with an acylating agent of formula $R^2(C=O)$—X', wherein $R^2$ is as defined above and X' is halo, $R^2(C=O)$—O—, or other suitable group in an acylating agent recognized by those of skill in the art, in the presence of an acid such as aluminum tribromide, aluminum trichloride, tin tetrachloride, titanium tetrachloride, or polyphosphoric acid, preferably aluminum tribromide, in a solvent such as dichloromethane, dichloroethane, nitromethane, nitrobenzene, carbon disulfide, or chlorobenzene, preferably dichloromethane, at a temperature between −20° C. and 125° C., preferably between 0 and 20° C., for a period between 10 minutes to 10 hours, preferably about 1 hour, to afford a compound of formula VII.

Step 2 of scheme 2 is the addition of a trifluoromethyl group to a ketone using a modification of a known method (Prakash, G. K. S.; Krishnamurti, R.; Olah, G. A. *J. Am. Chem. Soc.* 1989, 111, 393–395). Ketone of formula VII is treated with a compound of formula $CF_3SiR^4_3$, wherein $R^4$ is defined above, in the presence of a fluoride source such as cesium fluoride, potassium fluoride, or an alkylammonium fluoride such as tetrabutylammonium fluoride, preferably cesium fluoride, in the presence of a solvent such as dimethylformamide, dimethylacetamide, toluene, dichloromethane, dichloroethane, or tetrahydrofuran, preferably dimethylformamide, at a temperature between −78° C. and 50° C. preferably at room temperature, for a period of time between 10 minutes and 18 hours, preferably 45 minutes, to afford a compound of formula VIII.

Step 3 of scheme 2 is the deprotection of an alcohol. A compound of formula VIII is treated with a reagent such as sodium hydroxide, potassium hydroxide, or a fluoride source such at tetrabutylammonium fluoride, cesium fluoride, hydrofluoric acid-pyridine complex, or hydrofluoric acid, preferably tetrabutylammonium fluoride, in a solvent such as tetrahydrofuran, diisopropyl ether, acetonitrile, methyl-tert-butyl ether, dichloromethane, or toluene, preferably tetrahydrofuran, at a temperature between −40 and 60° C., preferably room temperature, for a period of time between 5 minutes and 5 hours, preferably one hour, to afford a compound of formula IX.

Step 4 of scheme 2 is the hydrolysis of an ester. A compound of formula IX is treated with a reagent such as sodium hydroxide, potassium hydroxide, sodium carbonate, sodium bicarbonate, potassium carbonate, potassium bicarbonate, preferably sodium hydroxide, in a solvent such as water, tetrahydrofuran, methanol, ethanol, isopropanol, 1,4-dioxane, or a combination of the above solvents, preferably a mixture of water and tetrahydrofuran, at a temperature between 0 and 75° C., preferably room temperature, for a period of time between 1 and 48 hours, preferably 12 hours, to afford a compound a formula X.

Step 5 of scheme 2 is a cyclization. A compound of formula X is treated with an activating agent such as methanesulfonyl chloride, methanesulfonic anhydride, p-toluenesulfonyl chloride, p-toluenesulfonic anhydride, or triflic anhydride, preferably methanesulfonyl chloride, and a base such as triethylamine, diisopropylethylamine, 2,6-lutidine, pyridine, sodium hydroxide, potassium hydroxide, cesium carbonate, or potassium carbonate, preferably triethylamine, in a solvent such as dichloromethane, tetrahydrofuran, toluene, diisopropyl ether, or methyl-tert-butyl ether, preferably dichloromethane, at a temperature between −40 and 75° C., preferably between 0° C. and room temperature, for a period of time between one and 48 hours, preferably 12 hours, to afford a compound of formula II.

Step 1 of scheme 3 an acylation of an arene. An arene of formula XIX is treated with an acylating agent of formula $R^2(C=O)—X'$, wherein $R^2$ is as defined above and X' is halo, $R^2(C=O)—O—$ or other suitable group in an acylating agent recognized by those of skill in the art, in the presence of an acid, such as aluminum tribromide, aluminum trichloride, tin tetrachloride, titanium tetrachloride, or polyphosphoric acid, preferably aluminum tribromide, in a solvent such as dichloromethane, dichloroethane, nitromethane, nitrobenzene, carbon disulfide or chlorobenzene, preferably dichloromethane, at a temperature between −20° C. and 125° C., preferably between 0 and 20° C., for a period between 10 minutes to 10 hours, preferably about 1 hour, to afford a compound of formula XI.

Step 2 of scheme 3 is an esterification. A carboxylic acid of formula XI is treated with an alcohol of formula $R^1OH$, wherein $R^1$ is defined above, in the presence of an acid such as sulfuric acid, hydrochloric acid, hydrobromic acid, trifluoroacetic acid or methanesulfonic acid, preferably sulfuric acid, at a temperature between 0 and 100° C., preferably at room temperature, for a period between 10 minutes to 48 hours, preferably 16 hours, to afford a compound of formula XII.

Scheme 3

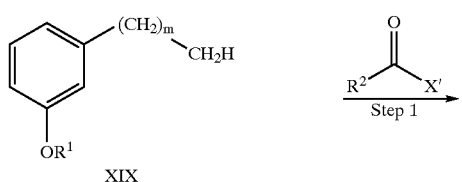

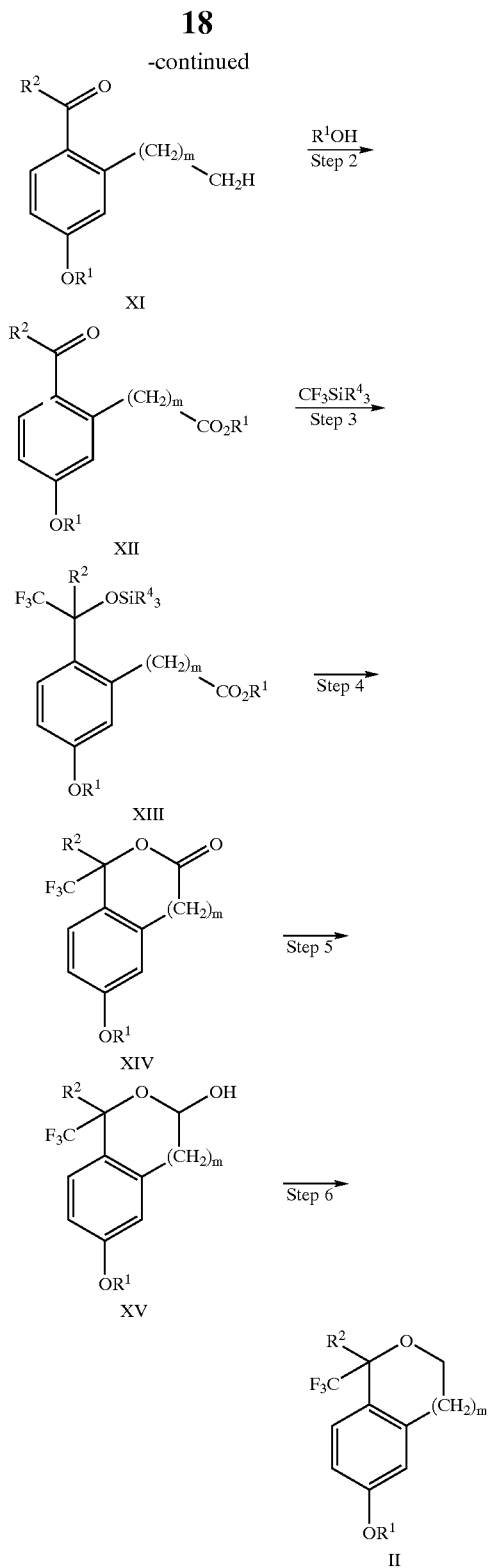

Step 3 of scheme 3 is the addition of a trifluoromethyl group to a ketone using a modification of a known method (Prakash, G. K. S.; Krishnamurti, R.; Olah, G. A. *J. Am. Chem. Soc.* 1989, 111, 393–395). Ketone of formula XII is treated with a compound of formula $CF_3SiR^4_3$, wherein $R^4$ is defined above, in the presence of a fluoride source such as cesium fluoride, potassium fluoride or an alkylammonium fluoride, such as tetrabutylammonium fluoride; preferably cesium fluoride, in the presence of a solvent such as dimethylformamide, dimethylacetamide, dichloromethane or tetrahydrofuran, preferably dimethylformamide, at a temperature between −78° C. and 50° C. preferably at 0° C., for a period of time between 10 minutes and 18 hours, preferably 7 hours, to afford a compound of formula XIII.

Step 4 of scheme 3 is a lactonization. A compound of formula XIII is treated with a fluoride source such at tetrabutylammonium fluoride, cesium fluoride, hydrofluoric acid-pyridine complex or hydrofluoric acid, preferably tetrabutylammonium fluoride, in a solvent such as tetrahydrofuran, diisopropyl ether, acetonitrile, methyl-tert-butyl ether, dichloromethane or toluene, preferably tetrahydrofuran, at a temperature between −40 and 60° C., preferably room temperature, for a period of time between 5 minutes and 5 hours, preferably one hour, to afford a compound of formula XIV.

Step 5 of scheme 3 is the reduction of a lactone. A compound of formula XIV is treated with a reducing agent such as sodium borohydride, borane tetrahydrofuran complex, borane dimethylsulfide complex, diborane, lithium borohydride, calcium borohydride, lithium aluminum hydride, diisobutylaluminum hydride, L-selectride or K-selectride, optionally in the presence of a Lewis acid, such as boron trifluoride diethyl ether complex; preferably sodium borohydride in the presence of boron trifluoride diethyl ether complex, in a solvent, such as tetrahydrofuran, diisopropyl ether, methyl-tert-butyl ether or dimethoxyethane, preferably tetrahydrofuran, at a temperature between −78 and 60° C., preferably between 0° C. and room temperature, for a period of time between 30 minutes and 48 hours, preferably 16 hours, to afford a compound of formula XV.

Step 6 of scheme 3 is a reduction. A compound of formula XV is treated with a reducing agent such as triethylsilane or triphenylsilane, in the presence of a Lewis acid such as boron trifluoride etherate or trifluoroacetic acid preferably trifluoroacetic acid, in a solvent such as dichloromethane, dichloroethane, or chloroform, preferably dichloromethane at a temperature between −78 and 60° C., preferably room temperature, for a period of time between 5 minutes and 5 hours, preferably 2 hours, to afford a compound of formula II. Alternatively, a compound of formula XV is treated with a reducing agent that is a catalyst, such as platinum, platinum oxide, or palladium hydroxide, preferably platinum, in a solvent such as methanol, ethanol, or isopropanol, preferably ethanol, under an atmosphere of hydrogen, optionally under pressure, at a temperature between room temperature and 100° C., preferably room temperature, for a period of time between 1 and 48 hours, preferably 5 hours, to afford a compound of formula II.

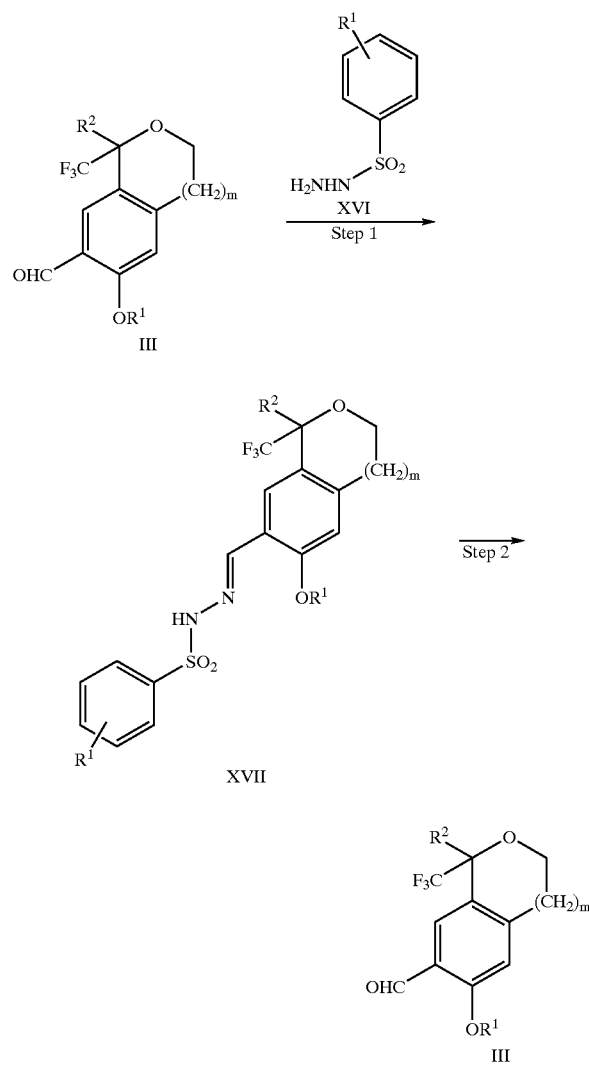

Scheme 4

Alternatively, compound III can be purified by derivatization. Step 1 of scheme 4 is the formation of a hydrazone. A compound of formula III is treated with a hydrazone of formula XVI with an acid such as acetic acid, sulfuric acid, hydrochloric acid, methanesulfonic acid or p-toluenesulfonic acid, preferably acetic acid, in a solvent such as methanol, ethanol, isopropanol, tetrahydrofuran, water or a mixture of any of the foregoing solvents, preferably a mixture of methanol and water, at a temperature between 0 and 110° C., preferably at reflux, for a period of time between 30 minutes and 10 hours, preferably 90 minutes, to afford a compound of formula XVII.

Step 2 of scheme 4 is the hydrolysis of a hydrazone. A compound of formula XVII is treated a reagent such as copper(II) chloride, copper(II) iodide, copper(II) acetate, copper sulfate, sulfuric acid, acetic acid or hydrochloric acid, preferably copper(II) chloride, in a solvent such as tert-butyl alcohol, methanol, ethanol, isopropanol, tetrahydrofuran, water or a mixture of any of the foregoing solvents, preferably a mixture of tert-butyl alcohol and water, at a temperature between 0 and 110° C., preferably at 70° C., for a period of time between 30 minutes and 10 hours, preferably 2.5 hours, to afford a compound of formula III.

The preparation of other compounds of the present invention not specifically described in the foregoing experimental section can be accomplished using combinations of the reactions described above that will be apparent to those skilled in the art.

In each of the reactions discussed or illustrated in Schemes 1–4 above, pressure is not critical, unless otherwise indicated. Pressures from about 0.9 atmospheres to about 2 atmospheres are generally acceptable and ambient pressure, i.e., about 1 atmosphere, is preferred as a matter of convenience.

Intermediate compounds of invention referred to above may contain chiral centers, and therefore may exist in different enantiomeric and diastereomeric forms; this invention is directed to all such optical and stereoisomers of said intermediate compounds, as well as mixtures thereof.

This invention is also directed to isotopically-labeled compounds identical to those recited in formulae Ia or Ib, or pharmaceutically acceptable salts thereof, but for the fact that one or more atoms are replaced therein by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

Compounds of the present invention, prodrugs thereof, and pharmaceutically acceptable salts of said compounds, or of said prodrugs, which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful, for example, in drug and/or substrate tissue distribution assays. Tritiated, i.e., $^{3}H$, and carbon-14, i.e., $^{14}C$, isotopes are particularly preferred for their ease of preparation and detectability. Furthermore, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances.

Isotopically labeled compounds of formulae Ia and Ib of this invention and prodrugs thereof can generally be prepared by carrying out the procedures set forth herein, by substituting a readily available isotopically labeled reagent for a non-isotopically labeled reagent.

The activity, methods for testing activities, dosages, dosage forms, methods of administration and background information concerning the compounds of formula Ia and Ib are set forth in International Patent Publication No. WO 99/25714, published May 27, 1999. The piperidinylaminomethyl trifluoromethyl cyclic ether compounds prepared by the methods of the present invention exhibit significant substance P receptor-binding activity and are of value in the treatment of a wide variety of clinical conditions which are characterized by the presence of an excess of said substance P activity. Such conditions include cardiovascular diseases, allergic disorders, angiogenesis, gastrointestinal disorders, central nervous system disorders, inflammatory diseases, emesis, urinary incontinence, pain, migraine, sunburn, and diseases, disorders and conditions caused by *Helicobacter pylori*, in a mammal, especially humans. For treatment of emesis, these compounds may preferably be used in combination with a 5-HT$_3$ antagonist.

The active piperidinylaminomethyl trifluoromethyl cyclic ether compounds of formulae Ia and Ib may be administered via either oral, parenteral (e.g., intravenously, intramuscularly or subcutaneously) or topical routes to mammals. These compounds may be administered alone or in combination with pharmaceutically acceptable carriers or diluents by any of the routes indicated above, and may be carried out in single or multiple doses. The compounds prepared by the methods of the invention may be administered in a wide variety of different dosage forms, e.g., combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups and the like.

EXAMPLES

The present invention is illustrated by the following examples. It will be understood, however, that the invention is not limited to the specific details of these examples.

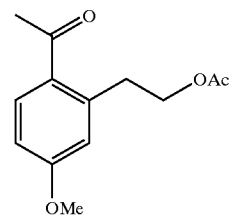

Acetic acid 2-(2-acetyl-5-methoxy-phenyl)-ethyl ester

This compound was prepared by modification of a known procedure. Sternberg, E. D.; Vollhardt, K. P. C. *J. Org. Chem.* 1984, 49, 1574–1583. To a solution of aluminum tribromide (43.8 g, 164 mmol) in dichloromethane (70 mL) at 0° C. was slowly added acetyl bromide (14.6 mL, 197 mmol). The reaction mixture was warmed to 15° C. and 2-(3-methoxy-phenyl)-ethanol (10.0 g, 65.7 mmol) in dichloromethane (20.0 mL) was added over 45 minutes. The reaction mixture was stirred for one hour and then poured over ice (100 mL). To the mixture was added 1N aqueous hydrochloric acid (100 mL). The organic layer was separated and the aqueous layer was extracted with dichloromethane (100 mL). The combined organic extracts were washed with IN aqueous sodium hydroxide (100 mL), dried over magnesium sulfate, filtered through Celite and concentrated to afford acetic acid 2-(2-acetyl-5-methoxy-phenyl)-ethyl ester as an oil (14.8 g, 95%). $^{1}H$ NMR (300 MHz, CDCl$_3$) δ2.05(s, 3), 2.59 (s, 3), 3.29 (t, 2, J=6.9), 3.89 (s, 3), 4.33 (t, 2, J=6.9), 6.81 (d, 1, J=2.5), 8.85 (dd, 1, J=8.6, 2.6), 7.82 (d, 1, J=8.6). $^{13}C$ NMR (75 MHz, CDCl$_3$) δ22.28, 30.37, 35.36, 56.63, 66.11, 101.21, 112.63, 119.17, 131.00, 134.23, 142.90, 163.24, 172.32. IR 1737, 1674, 1604, 1567, 1358, 1239, 1037 cm$^{-1}$. Analysis calculated for C$_{13}$H$_{16}$O$_4$: C, 66.09; H, 6.83. Found: C, 65.71; H, 7.21.

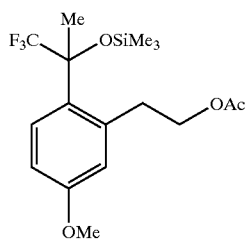

Acetic acid 2-[5-methoxy-2-(2,2,2-trifluoro-1-methyl-1-trimethylsilanyloxy-ethyl)-phenyl]-ethyl ester To a solution of acetic acid 2-(2-acetyl-5-methoxy-phenyl)-ethyl ester (12.5 g, 52.9 mmol) and cesium fluoride (0.964 g, 6.35 mmol) in dimethylformamide (75 mL) at 0° C. was slowly added trifluoromethyltrimethylsilane (10.2 mL, 69.0 mmol). The reaction mixture was stirred 45 minutes after which GS/MS and HPLC analysis showed no starting material. For characterization purposes, the reaction mixture was poured into water and extracted with methyl tert-butyl ether (100 mL). The organic layer was washed with water (2×75 mL) and brine (50 mL), dried over magnesium sulfate, filtered and concentrated to provide acetic acid 2-[5-methoxy-2-(2,2,2-trifluoro-1-methyl-1-trimethylsilanyloxy-ethyl)-phenyl]-ethyl ester as a crude oil. $^1$H NMR (300 MHz, CDCl$_3$) δ0.19 (s, 9), 1.93 (s, 3), 2.10 (s, 3), 3.23–3.33 (m, 1), 3.42–3.52 (m, 1), 3.83 (s, 3), 4.26–4.32 (m, 2), 6.77 (dd, 1, J=8.9, 2.8), 6.86 (d, 1, J=2.9), 7.32 (d, 1, J=8.9). $^{13}$C NMR (100 MHz, CDCl$_3$) δ2.03, 21.03, 24.64, 32.86, 55.11, 65.54, 78.90 (q, J=30.3), 111.26, 117.44, 125.70 (q, J=287), 129.56, 129.79, 139.77, 159.17, 171.09. IR 2961, 1741, 1610, 1383, 1286, 1255, 1165, 1140, 1039, 864, 846 cm$^{-1}$. Analysis calculated for C$_{17}$H$_{25}$F$_3$O$_4$Si: C, 53.95; H, 6.66. Found: C, 53.72; H, 6.53.

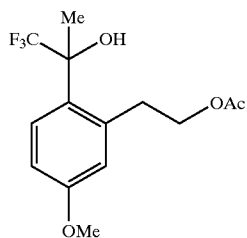

Acetic acid 2-[5-methoxy-2-(2,2,2-trifluoro-1-hydroxy-1-methyl-ethyl)-phenyl]-ethyl ester To the crude reaction mixture described in example 2 containing a solution of acetic acid 2-[5-methoxy-2-(2,2,2-trifluoro-1-methyl-1-trimethylsilanyloxy-ethyl)-phenyl]-ethyl ester was added tetrabutylammonium fluoride (52.9 mL of a 1.0M solution in tetrahydrofuran, 52.9 mmol). The reaction mixture was stirred one hour after which GC/MS and HPLC analysis showed no starting material. For characterization purposes, the reaction mixture was poured into water and extracted with methyl tert-butyl ether (75 mL). The organic layer was washed with water (75 mL) and brine (50 mL), dried over magnesium sulfate, filtered and concentrated to provide a crude oil. $^1$H NMR (400 MHz, CDCl$_3$) δ1.82 (s, 3), 2.01 (s, 3), 2.98–3.06 (m, 2), 3.55 (dt, 1, J=13.7, 6.8), 3.79 (s, 3), 4.27–4.34 (m, 2), 6.73–6.77 (m, 2), 7.28 (d, 1, J=8.5). $^{13}$C NMR (100 MHz, CDCl$_3$) δ20.92, 25.50, 34.16, 55.10, 66.49, 76.67 (q, J=30.3), 111.55, 118.25, 126.02 (q, J=286), 128.67, 129.56, 139.70, 159.20, 171.32. IR 3453, 1720, 1610, 1249, 1161, 1134, 1038 cm$^{-1}$. Analysis calculated for C$_{14}$H$_{17}$F$_3$O$_4$: C, 54.90; H, 5.59. Found: C, 55.03; H, 5.85.

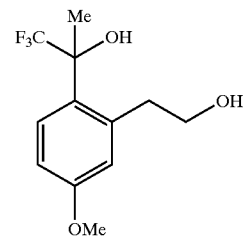

1,1,1-Trifluoro-2-[2-(2-hydroxy-ethyl)-4-methoxy-phenyl]-propan-2-ol

To the crude reaction mixture described in example 3 containing acetic acid 2-[5-methoxy-2-(2,2,2-trifluoro-1-hydroxy-1-methyl-ethyl)-phenyl]-ethyl ester was added 1N aqueous sodium hydroxide (75.0 mL, 75 mmol). The reaction mixture was allowed to warm to room temperature and was stirred 12 hours. The reaction mixture was poured into water (75 mL) and extracted with methyl tert-butyl ether (150 mL). The organic layer was washed with water (75 mL) and brine (75 mL), dried over magnesium sulfate, and concentrated to an oil. To the crude oil was added hexanes (20 mL) and methyl tert-butyl ether (4 mL) and a solid precipitated. The mixture was stirred for 30 minutes and filtered to provide 1,1,1-trifluoro-2-[2-(2-hydroxy-ethyl)-4-methoxy-phenyl]-propan-2-ol (7.3 g, 52% overall yield from acetic acid 2-(2-acetyl-5-methoxy-phenyl)-ethyl ester). M.p. 110–111° C. $^1$H NMR (300 MHz, CDCl$_3$) δ1.83 (s, 3), 2.91 (dt, 1, J=13.7, 3.9), 3.76 (ddd, 1, J=13.7, 9.3, 4.4), 3.85 (s, 3), 3.85–3.93 (m, 1), 4.08 (dt, 1, J 9.3, 3.7), 6.80–6.83 (m, 2), 7.38 (d, 1, J=8.4). $^{13}$C NMR (100 MHz, CDCl$_3$) δ26.01, 36.12, 55.19, 64.13, 76.52 (q, J=28.9), 111.47, 117.43, 125.99 (q, J=287), 129.69, 129.94, 140.86, 159.55. IR 3395, 3162, 1610, 1513, 1467, 1248, 1157, 1087, 1046 cm$^{-1}$. Analysis calculated for C$_{12}$H$_{15}$F$_3$O$_3$: C, 54.54; H, 5.72. Found: C, 54.65; H, 5.70.

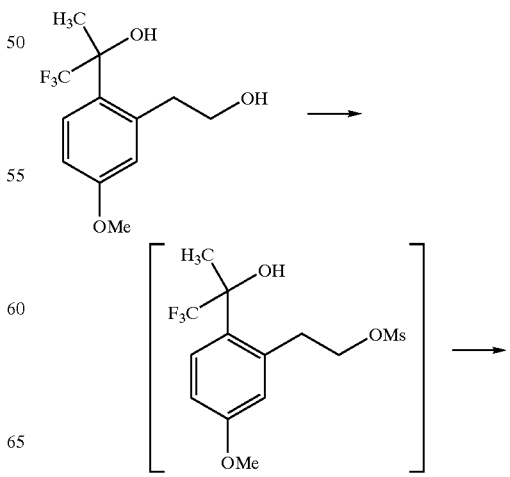

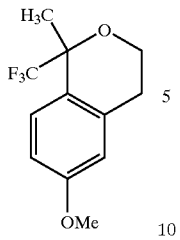

6-Methoxy-1-methyl-1-trifluoromethyl-isochroman

To a solution of 1,1,1-trifluoro-2-[2-(2-hydroxy-ethyl)-4-methoxy-phenyl]-propan-2-ol (5.00 g, 18.9 mmol) in dichloromethane (30 mL) was added triethylamine (9.20 mL, 66.3 mmol). The solution was cooled to 0° C. and methanesulfonyl chloride (1.61 mL, 20.8 mmol) was added dropwise. The reaction mixture was allowed to warm to room temperature and was stirred 12 hours. The formation of methanesulfonic acid 2-[5-methoxy-2-(2,2,2-trifluoro-1-hydroxy-1-methyl-ethyl)-phenyl]-ethyl ester is rapid and its disappearance was monitored by HPLC (retention time=4.5 minutes, Zorbax Rx-C6 column 4.6×150 mm, 40° C., 50% CH$_3$CN/50% (0.2% Et$_3$N, 0.1% H$_3$PO$_4$ aqueous pH=3.2 buffer), 1 mL/min). At the end of the reaction, the mixture was poured into 1N aqueous hydrochloric acid (30 mL) and was extracted with dichloromethane (20 mL). The organic extracts were dried over magnesium sulfate, filtered, and concentrated to afford 6-methoxy-1-methyl-1-trifluoromethyl-isochroman as an oil (3.40 g, 73%). $^1$H NMR (300 MHz, CDCl$_3$) δ1.69 (s, 3), 2.85–2.90 (m, 2), 3.85 (s, 3), 3.90–3.98 (m, 1), 4.14–4.21 (m, 1), 6.72 (d, 1, J=2.6), 6.85 (dd, 1, J=8.7, 2.6), 7.31 (d, 1, J=8.7). $^{13}$C NMR (100 MHz, CDCl$_3$) δ23.25, 29.42, 55.19, 61.37, 76.10 (q, J=27.4), 112.84, 113.43, 124.85, 125.96 (q, J=289), 127.86, 136.49, 158.98. IR 2946, 2839, 1738, 1611, 1505, 1162, 1137, 1101 cm$^{-1}$. Analysis calculated for C$_{12}$H$_{13}$F$_3$O$_2$: C, 58.54; H, 5.32. Found: C, 58.27; H, 5.35.

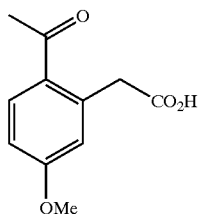

(2-Acetyl-5-methoxy-phenyl)-acetic acid

To a solution of aluminum tribromide (57.6 g, 216 mmol) in dichloromethane (90 mL) at 0° C. was slowly added acetyl chloride (11.5 mL, 162 mmol). To the reaction mixture was added (3-methoxy-phenyl)-acetic acid (17.9 g, 108 mmol) in dichloromethane (20.0 mL). The reaction mixture was stirred for one hour and then poured over ice (100 mL). The organic layer was separated and 1N aqueous sodium hydroxide was added (100 mL). The biphasic mixture was stirred vigorously for 90 minutes and the layers were separated. The organic layer was discarded and concentrated hydrochloric acid was added to the aqueous layer until the pH reached 1. A solid precipitated and was filtered and air-dried to afford (2-acetyl-5-methoxy-phenyl)-acetic acid (16.8 g, 75%). M.p. 153–155° C. $^1$H NMR (300 MHz, CDCl$_3$) δ2.68 (s, 3), 3.91 (s, 3), 3.92 (s, 2), 6.92–6.95 (m, 2), 7.88 (d, 1, J=9.5). $^{13}$C NMR (100 MHz, CDCl$_3$) δ28.33, 41.43, 55.46, 112.54, 118.26, 129.17, 133.08, 136.94, 162.65, 174.80, 200.96. IR 3435, 1704, 1663, 1609, 1568, 1258 cm$^{-1}$. Analysis calculated for C$_{11}$H$_{12}$O$_4$: C, 63.45; H, 5.81. Found: C, 63.35; H, 5.46.

(2-Acetyl-5-methoxy-phenyl)-acetic acid methyl ester

To a solution of (2-acetyl-5-methoxy-phenyl)-acetic acid (5.00 g, 24.0 mmol) in methanol (50 mL) was added concentrated sulfuric acid (1.0 mL). The reaction mixture was stirred at room temperature for 16 hours after which it was concentrated to a low volume. Dichloromethane (50 mL) was added and the solution was washed with 1N sodium hydroxide (50 mL). The layers were separated and the organic layer was dried over magnesium sulfate, filtered, and concentrated to an oil which solidified on standing to afford (2-acetyl-5-methoxy-phenyl)-acetic acid methyl ester (4.70 g, 88%). M.p. 74–76° C. $^1$H NMR (300 MHz, CDCl$_3$) δ2.58 (s, 3), 3.74 (s, 3), 3.89 (s, 3), 3.95 (s, 2), 6.78 (d, 1, J=2.6), 6.89 (dd, 1, J=8.7, 2.6), 7.89 (d, 1, J=8.6). $^{13}$C NMR (75 MHz, CDCl$_3$) δ29.65, 42.35, 53.11, 56.69, 113.17, 120.00, 130.52, 134.39, 138.90, 163.54, 173.23, 200.35. IR 1739, 1665, 1605, 1568, 1321, 1247, 1165 cm$^{-1}$. Analysis calculated for C$_{12}$H$_{14}$O$_4$: C, 65.85; H, 6.35. Found: C, 64.87; H, 6.44.

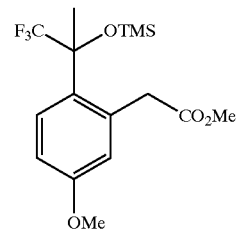

[5-Methoxy-2-(2,2,2-trifluoro-1-methyl-1-trimethylsilanyloxy-ethyl)-phenyl]-acetic acid methyl ester To a solution of (2-acetyl-5-methoxy-phenyl)-acetic acid methyl ester (2.00 g, 9.00 mmol) and cesium fluoride (96.0 mg, 0.632 mmol) in dimethylformamide (12 mL) at 0° C. was slowly added trifluoromethyltrimethylsilane (1.73 mL, 11.7 mmol). The reaction mixture was stirred at 0° C. for 7 hours. For characterization purposes, the reaction mixture was poured into water and extracted with methyl tert-butyl ether (50 mL). The organic layer was washed with water (2×75 mL) and brine (50 mL), dried over magnesium sulfate, filtered and concentrated to provide [5-methoxy-2-(2,2,2-trifluoro-1-methyl-1-trimethylsilanyloxy-ethyl)-phenyl]-acetic acid methyl ester as an oil. $^1$H NMR (400 MHz, CDCl$_3$) δ0.11 (s, 9), 1.89 (s, 2), 3.68 (s, 3), 3.77 (s, 3), 3.98 (d, 1, J=17.2), 4.28 (d, 1, J=17.0), 6.74–6.77 (m, 2), 7.29 (d, 1, J=9.1). $^{13}$C NMR (100 MHz, CDCl$_3$) δ1.87, 24.25, 39.32, 51.75, 55.12, 78.67 (q, J=30.3), 111.97, 118.30, 125.70 (q, J=286), 129.50, 129.57, 136.10, 159.17, 172.81. IR 2956, 1745, 1611, 1577, 1467, 1436, 1290, 1256, 1166, 1092, 989, 863, 847 cm$^{-1}$. Analysis calculated for $C_{16}H_{23}F_3O_4Si$: C, 52.73; H, 6.36. Found: C, 52.84; H, 6.36.

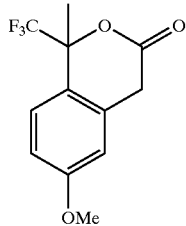

6-Methoxy-1-methyl-1-trifluoromethyl-isochroman-3-one

To the crude reaction mixture described in example 8 containing a solution of [5-methoxy-2-(2,2,2-trifluoro-1-methyl-1-trimethylsilanyloxy-ethyl)-phenyl]-acetic acid methyl ester was added tetrabutylammonium fluoride (9.00 mL of a 1.0M solution in tetrahydrofuran, 9.00 mmol). The reaction mixture was stirred for 1 hour after which it was poured into water (50 mL) and extracted with methyl tert-butyl ether (50 mL). The organic layer was washed with water (50 mL) and brine (30 mL), dried over magnesium sulfate, filtered, and concentrated to afford 6-methoxy-1-methyl-1-trifluoromethyl-isochroman-3-one as an oil (1.26 g, 54%). $^1$H NMR (400 MHz, CDCl$_3$) δ1.89 (s, 3), 3.71 (d, 1, J=20.6), 3.79 (s, 3), 3.89 (d, 20.8), 6.65 (d, 1, J=1.5), 6.85–6.89 (m, 1), 7.29 (d, 1, J=8.7). $^{13}$C NMR (100 MHz, CDCl$_3$) δ21.45, 34.32, 55.33, 83.01 (q, J=30.3), 112.21, 113.88, 120.57, 124.68 (q, J=285.7), 127.73, 132.18, 160.75, 167.45. IR 1765, 1614, 1509, 1322, 1301, 1274, 1259, 1183, 1101, 997, 813 cm$^{-1}$. Analysis calculated for $C_{12}H_{11}F_3O_3$: C, 55.39; H, 4.26. Found: C, 55.03; H, 4.54.

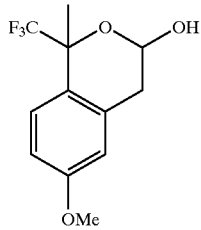

6-Methoxy-1-methyl-1-trifluoromethyl-isochroman-3-ol

To a solution 6-methoxy-1-methyl-1-trifluoromethyl-isochroman-3-one (1.50 g, 5.76 mmol) in tetrahydrofuran (30 mL) at 0° C. was added sodium borohydride (0.240 g, 6.34 mmol) followed by boron trifluoride diethyl ether complex (0.992 g, 8.07 mmol). The reaction mixture was warmed to room temperature and was stirred overnight. The reaction mixture was added to water (75 mL) and extracted with methyl-tert-butyl ether (75 mL). The layers were separated and the organic layer was washed with 1N aqueous hydrochloric acid (50 mL), dried over magnesium sulfate, filtered, and concentrated to afford 6-methoxy-1-methyl-1-trifluoromethyl-isochroman-3-ol as an oil and a mixture of a and b anomers (1.19 g, 79%). Data reported for the major diastereoisomer. $^1$H NMR (400 MHz, CDCl$_3$) δ1.74 (s, 3), 2.85 (dd, 1, J=15.7, 4.3), 2.88–2.99 (m, 1), 3.11 (dd, 1, J=15.7, 3.2), 3.80 (s, 3), 5.63 (t, 1, J=3.7), 6.69 (d, 1, J=2.7), 6.82 (dd, 1, J=8.7, 2.7), 7.22–7.27 (m, 1). $^{13}$C NMR (100 MHz, CDCl$_3$, data reported for identifiable signals of the major diastereoisomer) δ24.52, 35.46, 55.16, 90.71, 113.11, 113.98, 125.22, 127.57, 132.98, 159.59. IR 3439, 2949, 1735, 1613, 1506, 1166, 1141, 1070cm$^{-1}$

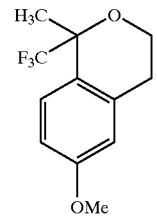

6-Methoxy-1-methyl-1-trifluoromethyl-isochroman

To a solution of 6-methoxy-1-methyl-1-trifluoromethyl-isochroman-3-ol (8.36 g, 31.9 mmol) in dichloromethane (84 mL) was added triethylsilane (15.3 mL, 95.8 mmol) followed by trifluoroacetic acid (14.7 mL, 191 mmol). The reaction was stirred at room temperature for 2 hours and was poured into 1N aqueous sodium hydroxide (250 mL). The organic layer was separated and washed with 1N aqueous sodium hydroxide (100 mL). The organic layer was dried over magnesium sulfate, filtered, and concentrated to afford 6-methoxy-1-methyl-1-trifluoromethyl-isochromanas an oil (6.88 g, 88%). $^1$H NMR (300 MHz, CDCl$_3$) δ1.69 (s, 3), 2.85–2.90 (m, 2), 3.85 (s, 3), 3.90–3.98 (m, 1), 4.14–4.21 (m, 1), 6.72 (d, 1, J=2.6), 6.85 (dd, 1, J=8.7, 2.6), 7.31 (d, 1, J=8.7). $^{13}$C NMR (100 MHz, CDCl$_3$) δ23.25, 29.42, 55.19, 61.37, 76.10 (q, J=27.4), 112.84, 113.43, 124.85, 125.96 (q, J=289), 127.86, 136.49, 158.98. IR2946, 2839, 1738, 1611, 1505, 1162, 1137, 1101 cm$^{-1}$. Analysis calculated for $C_{12}H_{13}F_3O_2$: C, 58.54; H, 5.32. Found: C, 58.27; H, 5.35.

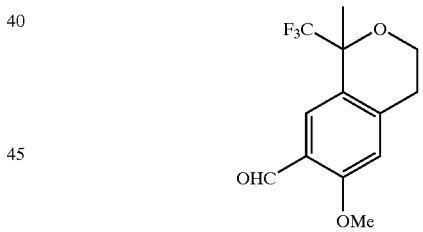

6-Methoxy-1-methyl-1-trifluoromethyl-isochroman-7-carbaldehyde

To hexamethylenetetramine (31.3 g, 223 mmol) was added trifluoroacetic acid (400 mL) and the mixture was heated to 70° C. for 90 minutes. A solution of 6-methoxy-1-methyl-1-trifluoromethyl-isochroman (50.0 g, 203 mmol) in trifluoroacetic acid (100 mL) was then added to the reaction mixture over 40 minutes. The solution was stirred for 3 hours and water was added (450 mL). The reaction mixture was stirred 16 hours, cooled to room temperature, and poured into methyl tert-butyl ether (500 mL). The organic layer was separated and washed with water (3×300 mL). The organic layer was poured into a round bottom flask and cooled to 0° C. 6N Sodium hydroxide was added in portions until the pH raised to 10 (~500 mL). The organic layer was separated, washed with water (200 mL), dried over magnesium sulfate, filtered, and concentrated to afford 6-methoxy-1-methyl-1-trifluoromethyl-isochroman-7-carbaldehyde as an oil (54.2 g of a 12:1 mixture of regioisomers, 97%). $^1$H NMR (400 MHz, CDCl$_3$) δ1.71 (s, 3), 2.95 (dt, 2, J=2.6, 5.3), 3.90–3.97 (m, 1), 3.97 (s, 3), 4.19 (dt, 1, J=11.2, 5.6), 6.81 (d, 1, J=1.2), 10.4 (s, 1). $^{13}$C NMR (75 MHz, CDCl$_3$) δ23.07, 29.98, 55.73, 60.83, 76.03 (q, J=27.4), 111.81, 112.50, 123.65, 125.32, 125.64 (q, J=287), 127.06, 160.89, 188.92. IR 1683, 1616, 1498, 1296, 1271, 1163, 1149, 1120, 1096, 874 cm$^{-1}$. Analysis calculated for C$_{13}$H$_{13}$F$_3$O$_3$: C, 57.13; H, 5.05. Found: C, 56.94; H, 4.78.

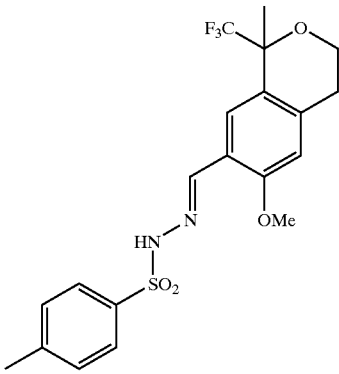

N'-1-[(E)-1-(6-Methoxy-1,1-dimethyl-3,4-dihydro-1H-isochromen-7-yl)methylidene]-4-methyl-1-benzenesulfonohydrazide To a solution of the crude 6-methoxy-1-methyl-1-trifluoromethyl-isochroman-7-carbaldehyde (54.2 g, 198 mmol) obtained from example 12 in methanol (542 mL) was added p-toluenesulfonhydrazide (36.9 g, 198 mmol) followed by 2% aqueous acetic acid (81.3 mL). The reaction mixture was heated to reflux for 90 minutes and cooled to room temperature. A solid precipitated and was filtered to provide N'-1-[(E)-1-(6-methoxy-1,1-dimethyl-3,4-dihydro-1H-isochromen-7-yl)methylidene]-4-methyl-1-benzenesulfonohydrazide (45.46 g, 52%). M.p.=181–183° C. $^1$H NMR (300 MHz, CDCl$_3$) δ1.71 (d, 3, J=0.7), 2.44 (s, 3), 2.85–2.89 (m, 2), 3.84 (s, 3), 3.93 (dt, 1,J=11.2, 5.6), 4.16 (dt, 1, J=11.2, 5.6), 6.65 (s, 1), 7.33 (d, 2, J=8.1), 7.79 (d, 1, J=1.2), 7.89 (d, 2, J=8.4), 8.13 (s, 1). $^{13}$C NMR (75 MHz, CDCl$_3$) δ21.48, 23.07, 29.50, 55.47, 60.99, 76.02 (q, J=27.4), 110.91, 120.45, 124.74, 125.04, 125.72 (q, J=287), 127.95, 129.45, 134.97, 138.97, 143.34, 144.22, 157.04. IR 3223, 1623, 1505, 1417, 1325, 1289, 1275, 1172, 1157, 1123, 1098, 918, 658 cm$^{-1}$. Analysis calculated for C$_{20}$H$_{21}$F$_3$N$_2$O$_4$S: C, 54.29; H, 4.78; N, 6.33. Found: C, 54.34; H, 4.73; N, 6.37.

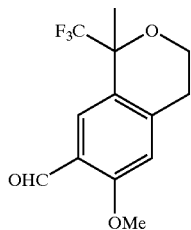

6-Methoxy-1-methyl-1-trifluoromethyl-isochroman-7-carbaldehyde

A mixture of copper (II) chloride (52.7 g, 309 mmol) and N'-1-[(E)-1-(6-methoxy-1,1-dimethyl-3,4-dihydro-1H-isochromen-7-yl)methylidene]-4-methyl-1-benzenesulfonohydrazide (45.5 g, 103 mmol) in tert-butyl alcohol (910 mL) and water (228 mL) was heated to 70° C. for 2.5 hours. The reaction mixture was cooled to room temperature, concentrated to about 300 mL and poured into methyl tert-butyl ether (500 mL) and water (500 mL). The mixture was stirred 15 minutes and filtered. The filtrate was poured into methyl tert-butyl ether (200 mL) and the layers were separated. The organic layer was washed with water (4×250 mL), dried over magnesium sulfate, filtered, and concentrated to provide 6-methoxy-1-methyl-1-trifluoromethyl-isochroman-7-carbaldehyde as an oil which solidified on standing (26.8 g, 95%). M.p.=82–93° C. $^1$H NMR (400 MHz, CDCl$_3$) δ1.71 (s, 3), 2.95 (dt, 2, J=2.6, 5.3), 3.90–3.97 (m, 1), 3.97 (s, 3), 4.19 (dt, 1, J=11.2, 5.6), 6.81 (d, 1, J=1.2), 10.4 (s, 1). $^{13}$C NMR (75 MHz, CDCl$_3$) δ23.07, 29.98, 55.73, 60.83, 76.03 (q, J=27.4), 111.81, 112.50, 123.65, 125.32, 125.64 (q, J=287), 127.06, 160.89, 188.92. IR 1683, 1616, 1498, 1296, 1271, 1163, 1149, 1120, 1096, 874 cm$^{-1}$. Analysis calculated for C$_{13}$H$_{13}$F$_3$O$_3$: C, 57.13; H, 5.05. Found: C, 56.94; H, 4.78.

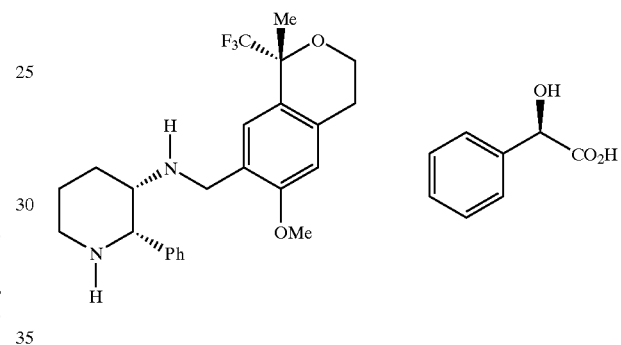

(2S,3S)-[(1R)-6-Methoxy-1-methyl-1-trifluoromethyl-isochroman-7-ylmethyl]-(2-phenyl-piperidin-3-yl)-amine (S)-(+)-mandelate Sodium triacetoxyborohydride (11.61 g, 54,8 mmol) was added in one portion to water bath chilled slurry of 6-methoxy-1-methyl-1-trifluoromethyl-isochroman-7-carbaldehyde (7.51 g, 27.4 mmol) and (2S-3S)-2-phenyl-piperidin-3-ylamine dimandelate (13.8 g, 28.7 mmol) in dichloromethane (150 mL). Within 15 minutes most starting material was dissolved and slow precipitation of product began shortly after. The reaction mixture was stirred 2.5 hour at room temperature, cooled to 0° C., and 1N aqueous sodium hydroxide (150 mL) was added slowly. The layers were separated, the aqueous layer (pH 9) was extracted with dichloromethane (50 mL). The combined organic extracts were stirred one hour with 1N aqueous sodium hydroxide (100 mL), the layers were separated and the organic layer was washed with water (50 mL), brine (50 mL), dried over Na$_2$SO$_4$. and filtered. The solvent was evaporated and the resulting off-white foam vacuum dried to give 11.08 g (93%) of the crude product. S-(+)Mandelic acid (7.55 g, 49.6 mmol) dissolved in ethanol (100 mL) was added to a solution of the mixture of diastereomers of (6-methoxy-1-methyl-1-trifluoromethyl-isochroman-7-ylmethyl)-(2-phenyl-piperidin-3-yl)-amine (10.78 g, 24.8 mmol) in ethanol (300 mL) at room temperature. The mixture was stirred and crystallization began to proceed. After stirring overnight, the mixture was filtered to yield 4.66 g (32% ) of (6-methoxy-1-methyl-1-trifluoromethyl-isochroman-7-ylmethyl)-(2-phenyl-piperidin-3-yl)-amine (S)-(+)-mandelate as a mixture of diastereomers (81:19 ratio by HPLC analysis). $^1$H NMR (400 MHz, CDCl₃ data reported for major diastereoisomer) δ1.42–1.64 (m, 2), 1.53 (s, 3), 1.72–1.79 (m, 1), 1.94–1.98 (m, 1), 2.46–2.89 (m, 4), 3.15–3.28 (m, 3), 3.45 (s, 3), 3.47–3.78 (m, 1), 3.92–3.97 (m, 2), 4.27 (bs, 1), 4.52 (s, 1), 6.66 (s, 1), 7.04–7.19 (m, 4), 7.27–7.36 (m, 7). ³C NMR (100 MHz, CDCl₃) δ16.99, 22.53, 25.96, 28.58, 45.05, 45.46, 53.52, 53.95, 55.08, 60.61, 61.86, 73.25, 75.54 (q, J=28.2), 110.36, 126.02, 126.27, 126.32, 126.42, 126.55, 127.01, 127.43, 127.57, 128.27, 135.04, 137.83, 143.16, 156.51, 174.59. IR 3441, 1576, 1358, 1160, 1136, 1098, 1038, 775, 756, 698 cm⁻¹. Analysis calculated for $C_{32}H_{37}F_3N_2O_5$: C, 65.52; H, 6.36; N, 4.78. Found: C, 65.55; H, 6.03; N, 4.84.

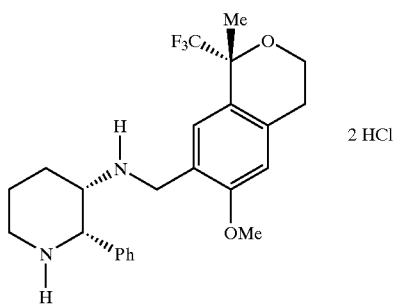

(2S,3S)[(1R)-6-Methoxy-1-methyl-1-trifluoromethyl-isochroman-7-ylmethyl]-(2-phenyl-piperidin-3-yl)-amine dihydrochloride (6-Methoxy-1-methyl-1-trifluoromethyl-isochroman-7-ylmethyl)-(2-phenyl-piperidin-3-yl)-amine (S)-(+)-mandelate (2.25 g of a 81:19 mixture of diastereoisomer, 3.84 mmol) was stirred overnight in diisopropyl ether (23 mL) and 1N aqueous sodium hydroxide (23 mL). The layers were separated and the organic layer washed with water (20 mL) and brine (20 mL). The organic layer was concentrated to a crude waxy solid and methanol (15 mL) was added. The solution was stirred at room temperature and a solution of 1.5N aqueous hydrochloric acid (5.0 mL) was added dropwise. The dihydrochloride salt precipitated immediately and the white slurry was stirred overnight at room temperature, filtered and dried under vacuum to afford (6-methoxy-1-methyl-1-trifluoromethyl-isochroman-7-ylmethyl)-(2-phenyl-piperidin-3-yl)-amine dihydrochloride (1.282 g, 66%) as a 96:4 mixture of diastereoisomers. The diastereomeric ratio could be further increase by crystallization from methanol/water (75/25). ¹H NMR (400 MHz, D₂O, data reported for major diastereoisomer) δ1.52 (s, 3), 1.80–1.92 (m, 2), 1.95–2.50 (m 1), 2.21–2.26 (m, 1), 2.63–2.71 (m, 2), 3.04–3.11 (m, 1), 3.36 (s, 3), 3.45–3.49 (m, 1), 3.65–3.81 (m, 3), 3.90–3.96 (m, 1), 4.09 (d, 1, J=13.5), 6.46 (s, 1), 6.98–7.07 (m, 3), 7.23–7.25 (m, 2), 7.30 (t, 1, J=7.5). IR 2958, 1457, 1377, 1143, 749, 692 cm⁻¹. Analysis calculated for $C_{24}H_{31}Cl_2F_3N_2O_2$: C, 56.81; H, 6.16; Cl, 13.97; N, 5.52. Found: C, 56.69; H, 6.31; Cl, 14.13; N, 5.55.

We claim:
1. A process for preparing a mixture of compounds of formulae Ia and Ib:

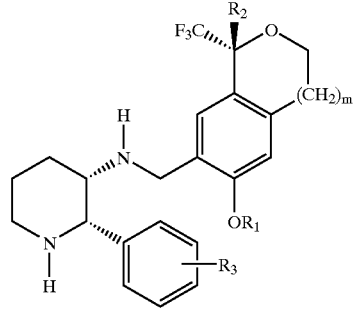

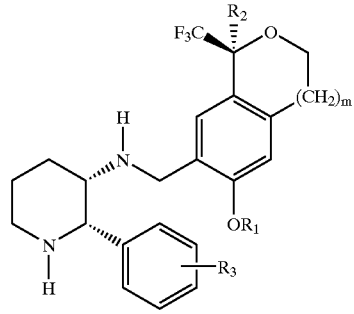

enriched in the compound of formula Ia, and pharmaceutically acceptable salts thereof, wherein
$R^1$ is $C_1$–$C_6$ alkyl;
$R^2$ is $C_1$–$C_6$ alkyl, halo $C_1$–$C_6$ alkyl or phenyl or substituted phenyl;
$R^3$ is hydrogen or halo;
m is zero, one or two;
comprising the steps of
(a1) reacting a mixture of compounds of formulae Ia and Ib:

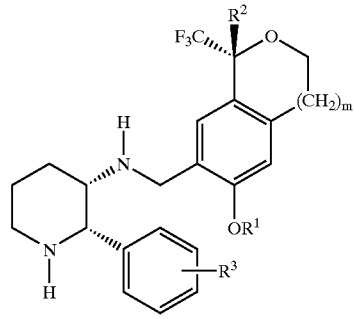

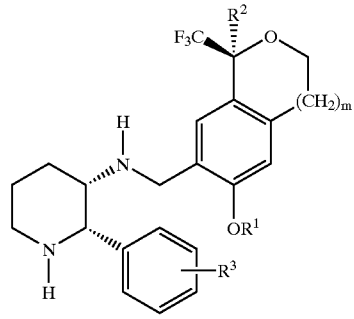

with an acid of formula HX, wherein HX is selected from the group consisting of (S)-(+)-mandelic acid, D-(−)-tartaric acid, di-p-toluoyl-D-tartaric acid, ((1R)-endo,anti)-(+)-3-bromocamphor-8-sulfonic acid, quinic acid, acetic acid and hydrobromic acid, to form a mixture of diastereomeric compounds of formulae Va and Vb, respectively:

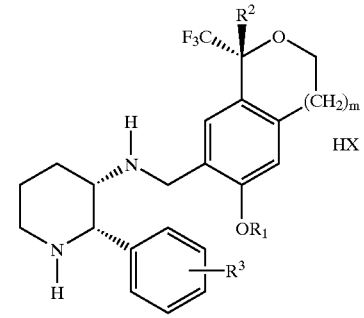

Va

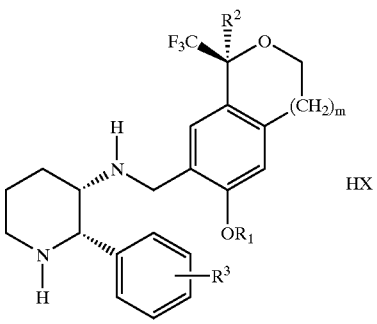

Vb (b1) permitting the HX salt of the diastereomeric product mixture of step (a1) to crystallize out of a solution thereof in an appropriate solvent;

(c1) treating the resulting mixture of compounds obtained from step (b1) with a base to obtain a mixture of compounds Ia and Ib, that is enriched in the compound of formula Ia.

2. A process according to claim 1 further comprising treating a mixture of compounds Ia and Ib, that is enriched in the compound of formula Ia:

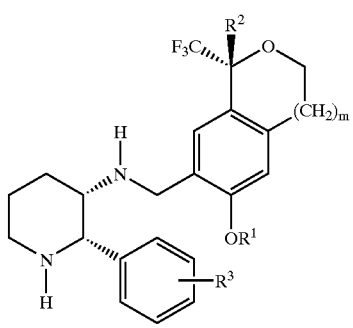

Ia

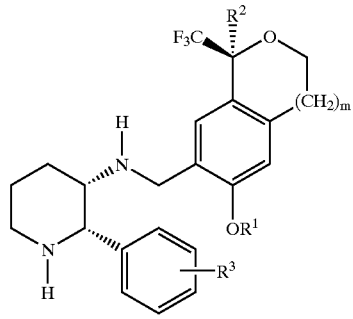

Ib with a proton acid, $H^+Y^-$, wherein the anion, $Y^-$, is selected from the group consisting of hydrochloride, hydrobromide, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and 1,1'-methylene-bis-(2-hydroxy-3-naphthoate), to form a mixture of compounds VIa and VIb, highly enriched in the diastereomeric compound acid addition salt of formula VIa:

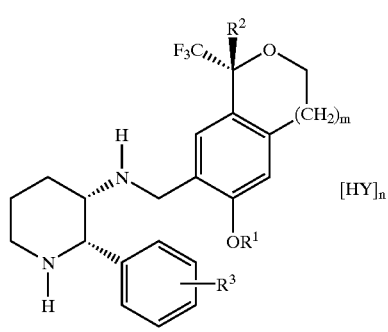

VIa

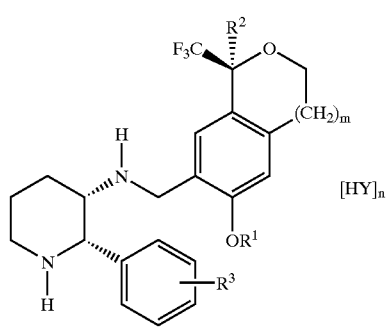

VIb wherein n is an integer from 1 to 2.

3. A process according to claim 2 wherein the proton acid is hydrochloric acid, and n is 2.

4. A process according to claim 1 wherein the acid HX of step (a1) is (S)-(+)-mandelic acid.

5. A process according to claim 1 wherein the base of step (c1) is selected from the group consisting of sodium hydroxide, potassium hydroxide, sodium carbonate, sodium bicarbonate, potassium carbonate or potassium bicarbonate, in water.

* * * * *